(12) United States Patent
Cervini

(10) Patent No.: US 9,936,886 B2
(45) Date of Patent: Apr. 10, 2018

(54) METHOD FOR THE ESTIMATION OF THE HEART-RATE AND CORRESPONDING SYSTEM

(71) Applicant: STMicroelectronics S.r.l., Agrate Brianza (IT)

(72) Inventor: Stefano Cervini, Sesto san Giovanni (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 170 days.

(21) Appl. No.: 14/724,579

(22) Filed: May 28, 2015

(65) Prior Publication Data

US 2015/0351646 A1  Dec. 10, 2015

(30) Foreign Application Priority Data

Jun. 9, 2014  (IT) .............................. TO2014A0462

(51) Int. Cl.
| | |
|---|---|
| *A61B 5/04* | (2006.01) |
| *A61B 5/02* | (2006.01) |
| *A61N 1/00* | (2006.01) |
| *A61B 5/024* | (2006.01) |
| *A61B 5/00* | (2006.01) |
| *A61B 5/11* | (2006.01) |

(52) U.S. Cl.
CPC ...... *A61B 5/02416* (2013.01); *A61B 5/02438* (2013.01); *A61B 5/11* (2013.01); *A61B 5/681* (2013.01); *A61B 5/6824* (2013.01); *A61B 5/721* (2013.01); *A61B 5/7225* (2013.01); *A61B 5/7257* (2013.01); *A61B 5/742* (2013.01); *A61B 2562/0219* (2013.01)

(58) Field of Classification Search
USPC ................................. 600/479, 301
See application file for complete search history.

(56) References Cited

U.S. PATENT DOCUMENTS

| | | |
|---|---|---|
| 6,262,943 B1 | 7/2001 | Clarke |
| 6,339,715 B1 | 1/2002 | Bahr et al. |
| 9,713,428 B2 | 7/2017 | Chon et al. |

(Continued)

FOREIGN PATENT DOCUMENTS

| | | |
|---|---|---|
| CN | 1269012 A | 10/2000 |
| CN | 1377485 A | 10/2002 |
| CN | 103596491 A | 2/2014 |
| CN | 205083467 U | 3/2016 |
| JP | 11-9564 | 1/1999 |

OTHER PUBLICATIONS

Han et al., "Development of real-time motion artifact reduction algorithm for a wearable photoplethysmography", Proceedings of the 29th Annual International Conference of the IEEE EMBS Cité Internationale, Lyon, France, Aug. 23-26, 2007, pp. 1538-1541.

(Continued)

*Primary Examiner* — Nicole F Johnson
(74) *Attorney, Agent, or Firm* — Seed IP Law Group LLP

(57) ABSTRACT

Method for the estimation of the heart-rate using photoplethysmography on a body organ, for example a wrist of a user, comprising acquiring optically from said body organ a heart beat signal, acquiring an acceleration signal representative of the acceleration of said body organ, selecting data blocks of said acquired heart beat signal and acceleration signal, compensating said heart beat signal by the acceleration signal, calculating the heart rate value on the basis of said compensated heart beat signal.

35 Claims, 8 Drawing Sheets

(56) References Cited

U.S. PATENT DOCUMENTS

| | | | |
|---|---|---|---|
| 2012/0150052 A1 | 6/2012 | Buchheim et al. | |
| 2014/0275854 A1* | 9/2014 | Venkatraman | A61B 5/721 600/301 |
| 2015/0065889 A1* | 3/2015 | Gandelman | A61B 5/02427 600/479 |
| 2015/0351646 A1 | 12/2015 | Cervini | |

OTHER PUBLICATIONS

Patterson, et al. "Ratiometric Artifact Reduction in Low Power Reflective Photoplethysmography", IEEE Transactions on Biomedical Circuits and Systems, vol. 5, No. 4, Aug. 2011, pp. 330-338.

Han et al., "Development of real-time motion artifact reduction algorithm for a wearable photoplethysmography," *Engineering in Medicine and Biology Society, 29th Annual International Conference of the IEEE*, 2007, 4 pages.

Kuboyama, *Motion artifact cancellation for wearable photoplethysmographic sensor*. Massachusetts Institute of Technology, 2010, 66 pages.

Reddy et al., "Motion artifact reduction in photoplethysmographic signals using singular value decomposition." *Instrumentation and Measurement Technology Conference Proceedings*, IEEE, 2007, 4 pages.

Wei et al., "A new wristband wearable sensor using adaptive reduction filter to reduce motion artifact." *Information Technology and Applications in Biomedicine, International Conference*, IEEE, 2008, 4 pages.

Chinese Office Action, dated Jul. 17, 2017, for Chinese Application No. 201510311911.0, 8 pages.

Chinese Search Report, dated Jul. 6, 2017, for Chinese Application No. 2015103119110, 2 pages.

* cited by examiner

METHOD FOR THE ESTIMATION OF THE HEART-RATE AND CORRESPONDING SYSTEM

BACKGROUND

Technical Field

The present description relates to techniques for the estimation of the heart-rate.

Various embodiments may apply, e.g., in wearable, in particular wrist-wearable devices, for continuous monitoring of the heart-rate in fitness/wellness applications.

Description of the Related Art

Among the methods for the estimation of the heart-rate in a subject, one of the most employed makes use of optical means to detect heart beat to evaluate the heart-rate, based on photoplethysmography (PPG). Photoplethysmography involves obtaining optically a volumetric measurement of an organ (plethysmogram). A photoplethysmogram is often obtained by using a pulse oximeter which illuminates the skin and measures changes in light absorption. A conventional pulse oximeter monitors the perfusion of blood to the dermis and subcutaneous tissue of the skin.

PPG was historically first employed with finger clips in medical applications. Lately PPG has been employed also on wrist, arm, forearm, to make it suitable for fitness applications.

The PPG techniques typically allow an easy estimation of the heart rate at rest. In motion conditions the PPG signal is affected however by a very low SNR (Signal to Noise Ratio) and SIR (Signal to Interference Ratio). In this specific context SNR means the ratio of the heart rate, e.g., the signal S indicative of the heart rate, to all the other signals, e.g., the noise N. It can be measured by having a subject wearing a cardio frequency meter and a PPG device. The power of the frequency component (peak) measured by the PPG device closest to cardio frequency measured by the cardio frequency meter is the signal S. The total power T is T=(S+N). Thus, for the SNR it is S/N=S/(T−S). The SIR value is obtained as ratio of the signal S over I, the power of the strongest non-cardiac frequency component.

Poor performances are sometimes obtained by processing a PPG signal with known frequency-domain techniques or time-domain techniques, including adaptive filtering techniques.

Thus problems affecting the PPG are strong motion artifacts leading to low SNR, low SIR due to motion artifacts, spikes in the detected signal due to motion.

In the state of the art it is known, in order to compensate the above discussed effects of motion on SNR and SIR and other aspect of the signal detection, to acquire optically from the body organ a heart rate signal, acquire an acceleration signal representative of the acceleration of such body organ, selecting data blocks of said acquired heart rate signal and acceleration signal, compensating in the time domain the heart rate signal by the acceleration signal.

The following publications described similar prior art techniques for the reduction of the artifacts:

Yuta Kuboyama, "Motion Artifact Cancellation for Wearable Photoplethismography Sensor", MIT, 2009;

K. Ashoka eddy, V. Jagadeesh Kumar, "Motion Artifact Reduction in Photoplethysmographic Signals using Singular Value Decomposition", Instrumentation and Measurement Technology Conference, Poland, May 1-3, 2007;

H. Han, M. Kim, J. Kim, "Development of real-time motion artifact reduction algorithm for a wearable photoplethismography", Proceedings of the 29th Annual International Conference of the IEEE EMBS Cite Internationale, Lyon, France, Aug. 23-26, 2007;

P. Wei, R. Guo, J. Zhang, Y. T. Zhang, "A New Wristband Sensor Using Adaptive Reduction Filter to Reduce Motion Artifact", Proceedings of the 5th International Conference on Information Technology and Application in Biomedicine, Shenzen, China, May 30-31, 2008.

BRIEF SUMMARY

In an embodiment, a method for the estimation of the heart-rate using photoplethysmography on a body organ, in particular on a wrist of a user, comprises acquiring optically from said body organ a signal representative of the heart beat, acquiring an acceleration signal representative of the acceleration of said body organ, selecting data blocks of said acquired heart beat signal and acceleration signal, compensating said heart beat signal by the acceleration signal, calculating a heart-rate value on the basis of said compensated heart beat signal, wherein said method includes obtaining from said selected data blocks corresponding frequency domain data blocks for the heart beat signal and for the acceleration signal, said compensating operation includes performing a motion compensation in the frequency domain, compensating the frequency domain data blocks for the heart beat with the corresponding frequency domain data blocks for the acceleration signal. In an embodiment, said motion compensation includes subtracting from the frequency domain data blocks for the heart beat the frequency domain data blocks multiplied by a respective scalar weight to obtain said compensated heart beat signal. In an embodiment, the method includes performing a detection operation on said compensated heart beat signal to obtain an estimate of the heart rate. In an embodiment, the method includes computing a non-linear predictor value on the basis of said frequency domain data blocks, performing a correction operation of the detected estimate of the heart rate including performing a decision between the detected estimate of the heart rate and a predicted estimate to select a decided heart rate value, said predicted estimate being obtained as a linear function of said predictor. In an embodiment, said performing a decision between the detected estimate of the heart rate and a predicted estimate to select a decided heart rate value includes a smoothing operation applied taking in account a plurality of estimates at different times and averaging over them. In an embodiment, the method includes updating said linear function by storing the current detected estimate and predictor value each time the operation of performing a decision selects the optical estimate, obtaining a sequence of observation points, in particular stored in a FIFO, calculating the linear function as regression over said sequence of observation points. In an embodiment, the method includes performing an aggregation operation over said sequence of observation points to keep low their number. In an embodiment, the method includes performing a filtering before said selecting data blocks of said acquired heart beat signal and acceleration signal, in particular said filtering comprising a low-pass FIR filter and a high-pass filter, in particular implemented by a chain of IIR filters. In an embodiment, said selecting data blocks of said acquired heart beat signal and acceleration signal includes provisionally generating a data block from the acquired heart beat signal, testing a condition on said block and, in case the condition is met forwarding said block and the data blocks of said acquired acceleration signal, time-aligned with said data block from the acquired heart beat signal to the operation for obtaining corresponding frequency domain data blocks for the heart beat signal and for the acceleration signal, while, in case said condition is not met, generating a new provisional block that is time shifted relative to the previous block. In an embodiment, said motion compensation operation is followed by a detection operation to identify a main frequency of the compensated frequency domain heart beat signal which is outputted as detected heart rate estimate. In an embodiment, said operation of obtaining from said selected data blocks corresponding frequency domain data blocks for the heart beat signal and for the acceleration signal includes obtaining a plurality of bins by interleaving a plurality of Fast Fourier Transform operations.

In an embodiment, a system for the estimation of the heart-rate using photoplethysmography on a body organ, in particular a wrist of a user, comprises sensors configured for acquiring optically from said body organ a heart beat signal and acquiring an acceleration signal representative of the acceleration of said body organ and a processor module configured for selecting data blocks of said acquired heart beat signal and acceleration signal, compensating said heart beat signal by the acceleration signal, calculating the heart rate value on the basis of said compensated heart beat signal, wherein said module is configured to perform one or more embodiments of methods disclosed herein. In an embodiment, said sensors and said processing module are comprised in a same photoplethysmographic heart rate measuring device. In an embodiment, said device is comprised in a apparatus which is wearable on said body organ. In an embodiment, said wearable apparatus is wearable on the wrist or the arm, in particular by means of a bracelet. In an embodiment, the system comprises a remote processing device connected by a communication link with said photoplethysmographic heart rate measuring device. In an embodiment, wherein said photoplethysmographic heart rate measuring device includes a display. In an embodiment, a computer program product that can be loaded into the memory of at least one computer comprises parts of software code that are able to execute the steps of one or more embodiments of a method disclosed herein.

One or more embodiments may refer to a corresponding system, to a corresponding measuring device and as well as to a computer program product that can be loaded into the memory of at least one computer and comprises parts of software code that are able to execute the steps of the method when the product is run on at least one computer. As used herein, reference to such a computer program product is understood as being equivalent to reference to a computer-readable means containing instructions for controlling the processing system in order to co-ordinate implementation of the method according to the embodiments. Reference to "at least one computer" is evidently intended to highlight the possibility of the present embodiments being implemented in modular and/or distributed form.

The claims form an integral part of the technical teaching provided herein in relation to the various embodiments.

According to an embodiment described herein, the method comprises that said compensation operation includes obtaining from said selected data blocks corresponding frequency domain data blocks for the heart rate signal and acceleration signal, performing a motion compensation of the frequency domain data blocks for the heart rate using the frequency domain data blocks for the acceleration signal.

In various embodiments, the method comprises performing the motion compensation by subtracting from the frequency domain data blocks for the heart the frequency domain data blocks in the frequency by a scalar weight to obtain said compensated heart rate signal.

In various embodiments, the method comprises performing a detection operation on said compensated heart rate signal to obtain an estimate of the heart rate.

In various embodiments, the method comprises computing a non-linear predictor value on the basis of said frequency domain data blocks, performing a correction operation of the detected estimate of the heart rate including performing a decision between the detected estimate of the heart rate and a predicted estimate to select a heart rate value, said predicted estimate being obtained as a linear function of said predictor.

In various embodiments, the method comprises performing a decision which includes smoothing operations to obtain a final heart rate estimate.

In various embodiments, the system implementing the method comprises sensors configured for acquiring optically from said body organ a signal representative of the heartbeat and acquiring an acceleration signal representative of the acceleration of said body organ and a processor module configured for selecting data blocks of said acquired heart beat signal and acceleration signal, compensating said heart beat signal by the acceleration signal, calculating the heart rate value on the basis of said compensated heart beat signal.

In various embodiments, the system includes such sensors and processing module are comprised in a same photoplethysmographic heart rate measuring device.

In various embodiments, the PPG heart rate measuring device is comprised in an apparatus which is wearable on said body organ, in particular the apparatus is wearable on the wrist or the arm, in particular by means of a bracelet.

In various embodiments, it is provided a photoplethysmographic heart rate measuring device capable of operating in the system here described.

In various embodiments such device is associated to a remote processing device connected to it by a communication link.

In various embodiments such device includes a display.

In an embodiment, a method comprises: selecting heart-beat data blocks based on a received heart-beat signal; selecting acceleration data blocks based on one or more received acceleration signals; converting the selected heart-beat data blocks to heart-beat frequency domain data blocks; converting the selected acceleration data blocks to acceleration frequency domain data blocks; performing motion compensation in the frequency domain based on the converted frequency domain data blocks; and generating a heart-rate signal based on the motion compensation. In an embodiment, the method comprises generating the received heart-beat signal using photoplethysmography on a wrist. In an embodiment, said motion compensation includes: multiplying the acceleration frequency domain data blocks by respective scalar weights; and subtracting the weighted acceleration frequency domain data blocks from the heart-beat frequency domain data blocks. In an embodiment, the method comprises: generating a compensated heart-beat signal; and estimating a heart rate based on the compensated heart-beat signal. In an embodiment, the method comprises: computing a non-linear predictor value based on the acceleration frequency domain data blocks; generating a predicted estimate as a linear function of the predictor value; and generating the heart-rate signal based on the estimated heart rate and the predicted estimate. In an embodiment, the generating the heart-rate signal comprises selecting one of the estimated heart rate and the predicted estimate. In an embodiment, the method comprises: averaging a plurality of estimated heart rates estimated at different times. In an embodiment, the method comprises: updating said linear function by storing a current estimated heart rate and predictor value when the estimated heart rate is selected, obtaining a sequence of observation points; and calculating the linear function as a regression over said sequence of observation points. In an embodiment, the method comprises performing an aggregation operation over said sequence of observation points. In an embodiment, the method comprises: filtering the received heart-beat signal and selecting the heart-beat data blocks based on the filtered heart-beat signal; filtering the received one or more acceleration signals and selecting the acceleration data blocks based on the filtered one or more acceleration signals, the filtering including low-pass filtering and high-pass filtering, the high-pass filtering using a chain of infinite impulse response filters. In an embodiment, the method comprises: generating a data block based on the received heart-beat signal; determining whether the generated data block satisfies a testing condition; when the generated data block satisfies the testing condition, converting the generated data block and data blocks based on the received one or more acceleration signals which are time-aligned with said generated data block to frequency domain data blocks; and when the generated data block does not satisfy the testing condition, discarding the generated data block and generating a new data block that is time-shifted relative to the previously generated data block. In an embodiment, the estimating the heart rate comprises identifying a frequency of the compensated heart-beat signal. In an embodiment, the method comprises: interleaving a plurality of Fast Fourier Transform operations.

In an embodiment, a device comprises: an interface configured to receive a heart-beat signal and one or more acceleration signals: and signal processing circuitry configured to: select heart-beat data blocks based on the heart-beat signal; select acceleration data blocks based on the one or more acceleration signals; convert the selected heart-beat data blocks to heart-beat frequency domain data blocks; convert the selected acceleration data blocks to acceleration frequency domain data blocks; perform motion compensation in the frequency domain based on the converted frequency domain data blocks; and generate a heart-rate signal based on the motion compensation. In an embodiment, the device comprises: one or more light sources; and one or more optical sensors configured to generate the heart-beat signal. In an embodiment, the signal processing circuitry is configured to: multiply the acceleration frequency domain data blocks by respective scalar weights; and subtract the weighted acceleration frequency domain data blocks from the heart-beat frequency domain data blocks. In an embodiment, the signal processing circuitry is configured to: generate a compensated heart-beat signal; and estimate a heart rate based on the compensated heart-beat signal. In an embodiment, the signal processing circuitry is configured to: compute a non-linear predictor value based on the acceleration frequency domain data blocks; generate a predicted estimate as a linear function of the predictor value; and generate the heart-rate signal based on the estimated heart rate and the predicted estimate. In an embodiment, the signal processing circuitry is configured to select one of the estimated heart rate and the predicted estimate. In an embodiment, the signal processing circuitry is configured to: average a plurality of estimated heart rates estimated at different times. In an embodiment, the signal processing circuitry is configured to: update said linear function by storing a current estimated heart rate and predictor value when the estimated heart rate is selected, obtaining a sequence of observation points; and calculate the linear function as a regression over said sequence of observation points. In an embodiment, the signal processing circuitry comprises: a plurality of low-pass filters and a plurality of high-pass filters configured to filter the received signals. In an embodiment, the signal processing circuitry is configured to: generate a data block based on the received heart-beat signal; determine whether the generated data block satisfies a testing condition; when the generated data block satisfies the testing condition, convert the generated data block and data blocks based on the received one or more acceleration signals which are time-aligned with said generated data block to frequency domain data blocks; and when the generated data block does not satisfy the testing condition, discard the generated data block and generate a new data block that is time-shifted relative to the previously generated data block.

In an embodiment, a system comprises: an optical sensor configured to generate a heart-beat signal; an accelerometer configured to generate one or more acceleration signals; and signal processing circuitry configured to: select heart-beat data blocks based on the heart-beat signal; select acceleration data blocks based on the one or more acceleration signals; convert the selected heart-beat data blocks to heart-beat frequency domain data blocks; convert the selected acceleration data blocks to acceleration frequency domain data blocks; perform motion compensation in the frequency domain based on the converted frequency domain data blocks; and generate a heart-rate signal based on the motion compensation. In an embodiment, the system comprises: an integrated circuit including the signal processing circuitry. In an embodiment, the integrated circuit includes the optical sensor and the accelerometer. In an embodiment, the system comprises: a transmitter configured to transmit the generated heart-rate signal; and a receiver configured to receive the transmitter heart-rate signal. In an embodiment, the system comprises a display.

In an embodiment, a non-transitory computer-readable medium's contents configure a heart-rate monitoring device to perform a method, the method comprising: selecting heart-beat data blocks based on a received heart-beat signal; selecting acceleration data blocks based on one or more received acceleration signals; converting the selected heart-beat data blocks to heart-beat frequency domain data blocks; converting the selected acceleration data blocks to acceleration frequency domain data blocks; performing motion compensation in the frequency domain based on the converted frequency domain data blocks; and generating a heart-rate signal based on the motion compensation. In an embodiment, the method comprises: multiplying the acceleration frequency domain data blocks by respective scalar weights; and subtracting the weighted acceleration frequency domain data blocks from the heart-beat frequency domain data blocks. In an embodiment, the method comprises: generating a compensated heart-beat signal; and estimating a heart rate based on the compensated heart-beat signal. In an embodiment, the method comprises: computing a non-linear predictor value based on the acceleration frequency domain data blocks; generating a predicted estimate as a linear function of the predictor value; and generating the heart-rate signal based on the estimated heart rate and the predicted estimate.

BRIEF DESCRIPTION OF THE SEVERAL VIEWS OF THE DRAWINGS

Example embodiments will now be described purely by way of a non-limiting example with reference to the annexed drawings, in which.

DETAILED DESCRIPTION

The ensuing description illustrates various specific details aimed at an in-depth understanding of the embodiments. The embodiments may be implemented without one or more of the specific details, or with other methods, components, materials, etc. In other cases, known structures, materials, or operations are not illustrated or described in detail so that various aspects of the embodiments will not be obscured.

Reference to "an embodiment" or "one embodiment" in the framework of the present description is meant to indicate that a particular configuration, structure, or characteristic described in relation to the embodiment is comprised in at least one embodiment. Likewise, phrases such as "in an embodiment" or "in one embodiment", that may be present in various points of the present description, do not necessarily refer to the one and the same embodiment. Furthermore, particular conformations, structures, or characteristics can be combined appropriately in one or more embodiments.

The references used herein are intended merely for convenience and hence do not define the sphere of protection or the scope of the embodiments.

Figure 1A:
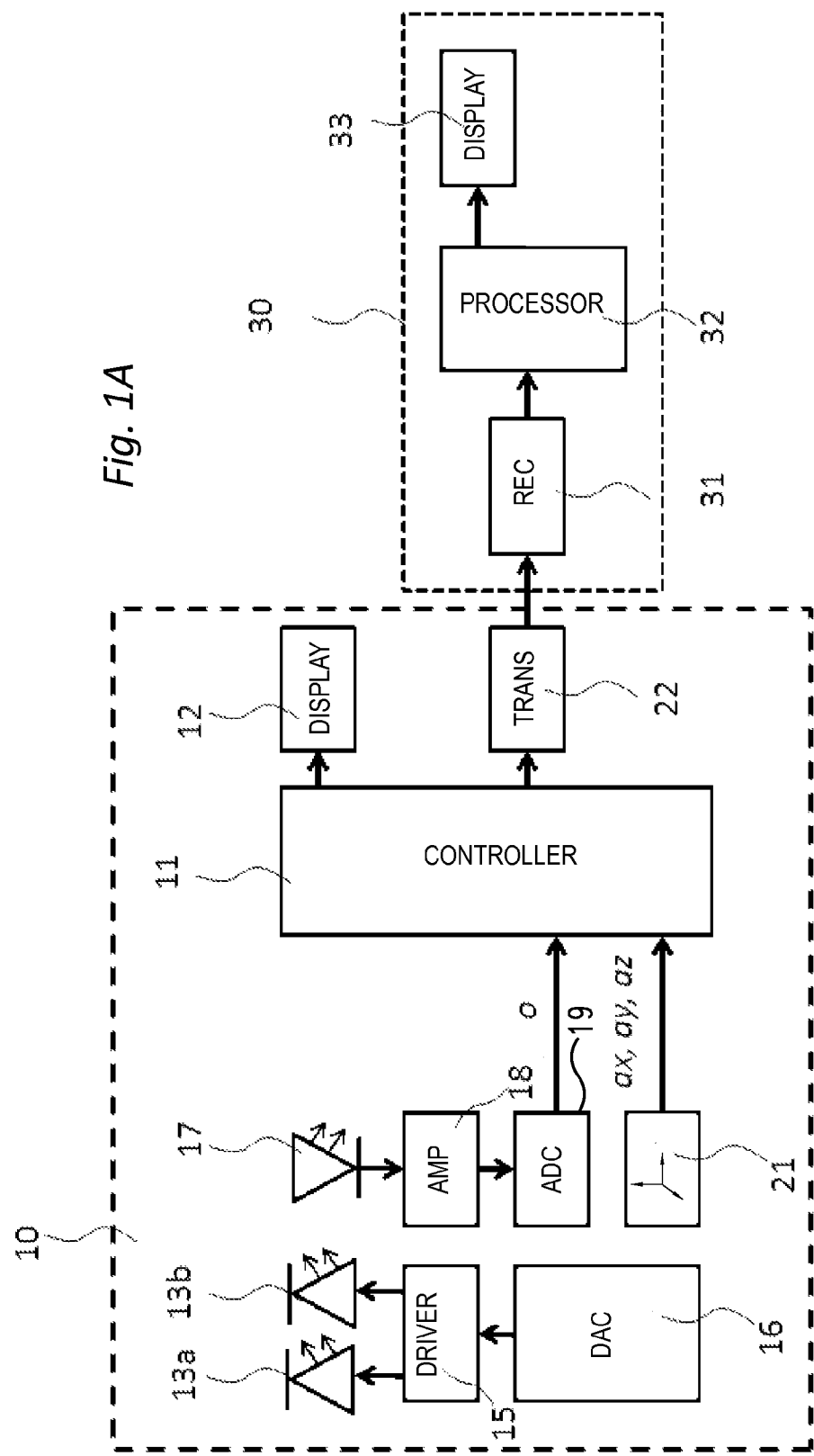
FIGS. 1A and 1B show a system and a device operating according to an embodiment of a method for estimation of the heart rate.

In FIG. 1A it is shown a block diagram representing a photoplethysmographic (PPG) device 10 for measuring the heart rate. Such PPG device 10 includes two lighting emitting diodes, e.g., LEDs, 13a and 13b, for example green LEDs, which emit light in the direction of the user's skin surface. Such LEDs 13a and 13b are driven by a LED driver 15 which is in its turn controlled by a digital to analog converter 16 to control the current value. The skin surface is the skin surface of a body organ which may be, for example, the wrist. Other suitable body organs can be for instance the arm, the forearm, the finger, the forehead or the ear. Light is absorbed, reflected, scattered, and transmitted as it travels through the user's tissues and encounters one or more blood vessels. Heart beats cause the amount of light reflected to drop during systoles and to increase during diastoles. The reflected light is sensed by a photodiode 17 which converts the amount of light into a current. The two LEDs 13a and 13b may, for example, be placed respectively immediately above and below the photodiode 17. The current at the output of photodiode 17 is converted into a voltage by means of a trans-impedance amplifier 18. Finally the voltage is converted into a digital word by means of an analog-to-digital converter 19, for instance a 12-bit analog-to-digital converter 19 operating at a sampling rate $f_s$ of 100 Hz and acquired by a microcontroller 11, for example a 32-bit microcontroller STM32L1 (or STM32F), as a optically acquired digital signal representative of the heart beat, or digital optical heart beat signal o. The microcontroller 11 also controls by means of one of its digital outputs connected to digital-to-analog converter 16 the current of the LEDs 13a and 13b, e.g., their light intensity.

The PPG device 10 includes also a three-axis accelerometer 21, which is, for example, equipped with an internal analog-to-digital converter operating at the same sampling rate $f_s$, 100 Hz, which provides three accelerometric signals to the microcontroller, namely ax, ay, az, according to axis x, y and z respectively.

Figure 2:
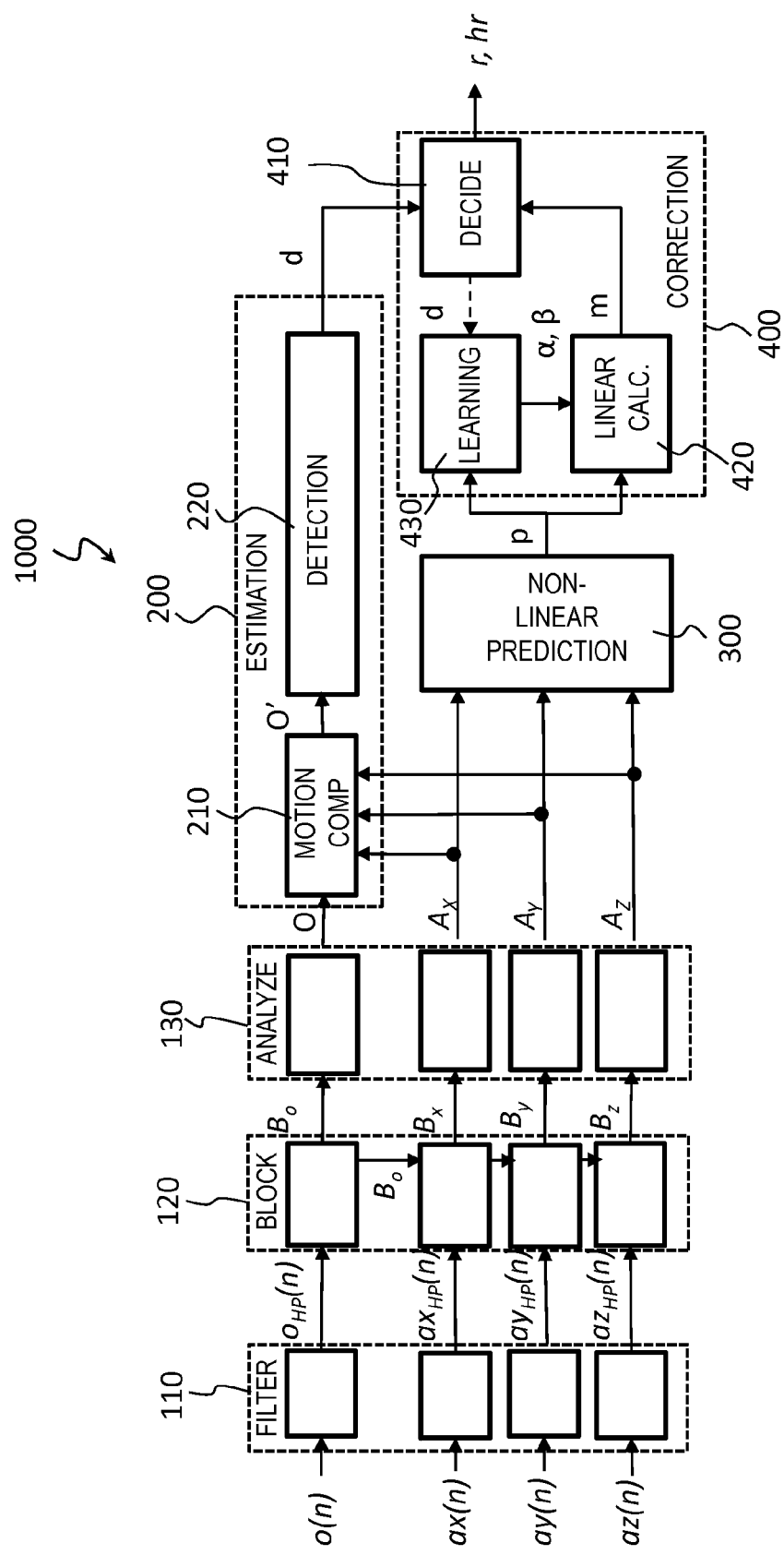
FIG. 2 represents a block diagram of the operations performed by said method.

An internal memory, in particular a SRAM, of the microcontroller 11, in particular the 48 KB SRAM of the STM32L1 microcontroller, may be used to implement the method for the estimation of the heart rate here described, indicated as a whole with reference 1000 in FIG. 2. Such method for the estimation of the heart rate receives as input the optically acquired heart beat signal o and the accelerometric signals ax, ay, az and supplies as output a series of heart rate estimate values r. If more memory is available, for example by using the alternative STM32F4 microcontroller, an operation of decimation during a filtering stage 110 shown in FIG. 2 may be avoided.

Figure 1B:
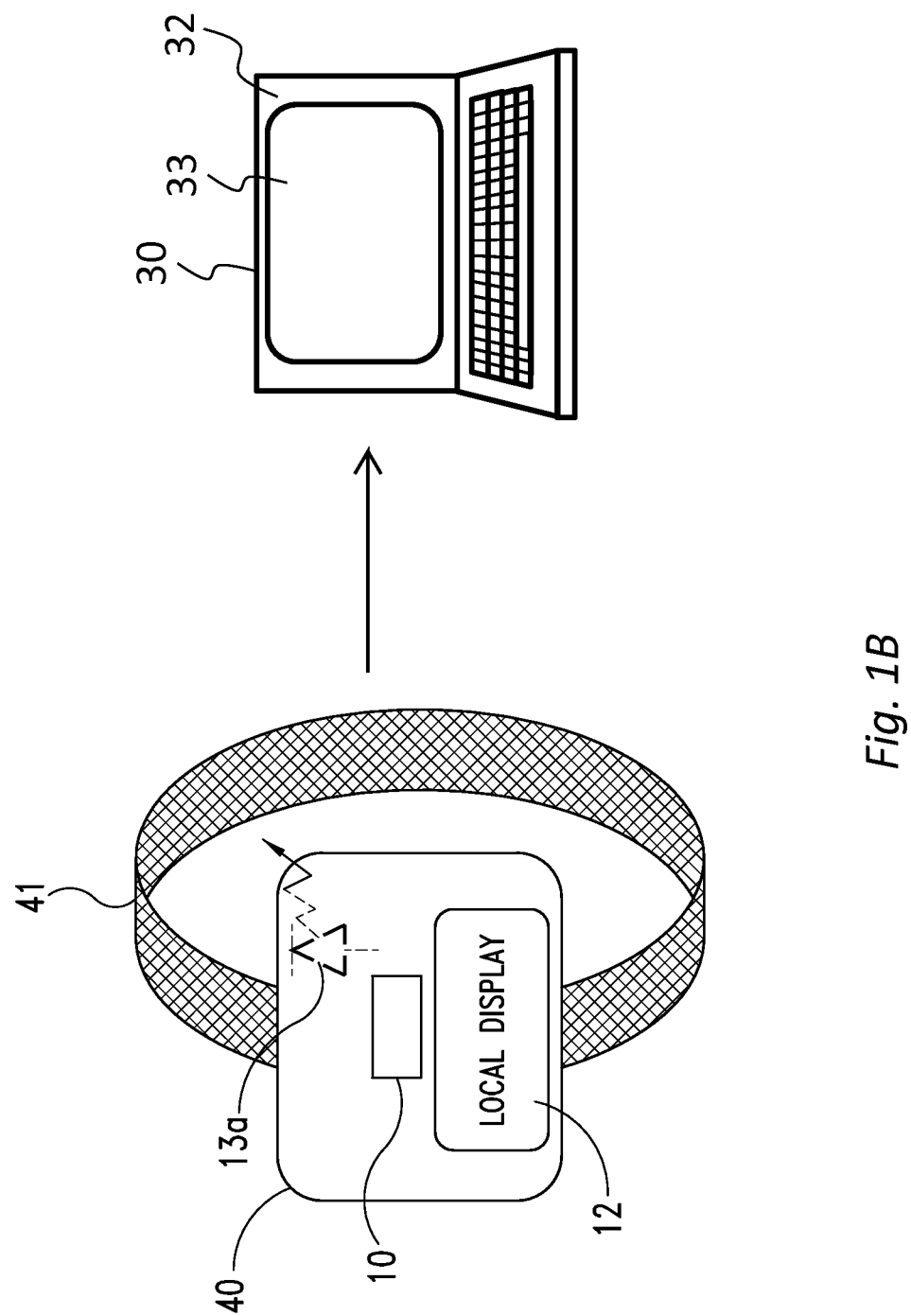

The PPG heart rate measuring device 10 in an embodiment, shown in FIG. 1B, is arranged in a wrist-wearable device 40, including a wrist bracelet 41, with the LEDs 13a and 13b and the photodiode PD oriented in direction of the wrist skin surface. In FIG. 1B for simplicity's sake only LED 13a is shown, in dashed line.

The PPG device 10 is equipped with an own local display 12 to visualize the series of heart rate estimate values r, in particular, as better detailed in the following, the time series r(n) of the heart rate estimates r. The microcontroller 11 itself can further use the data of the heart estimate r for statistics and other type of data manipulation, for instance in order to supply different types of data presentations to the user, such as statistical analyses, the microcontroller 11 itself can further perform processing of the heart rate estimate r, acting as a local application processor if it has enough computing power. Also, the PPG device 10 comprises a transmitter 22, in the example a Bluetooth transmitter, to send wirelessly the series of heart rate estimate values r to a remote device 30, also shown in FIG. 1, which receives the series of heart rate estimate values r by means of a corresponding receiver 31, which sends the data to an application processor 32, which in its turn shows the results on a display 33. The remote device 30 can be for instance a PC, as shown in FIG. 1B, or a smart phone or another device capable of processing and displaying data.

Such option of having the time series of the heart rate estimate values r either visualized on a local display 12, used by the microcontroller 11 itself or sent wirelessly to the remote device 30 depends on the product/application that the system is integrated onto.

In FIG. 2 it is shown a block diagram representing an embodiment of a method for the estimation of the heart rate, indicated as a whole with the reference 1000, which is performed by the microcontroller 11.

The digital optical heart beat signal o acquired by the PPG device 10 and the digital accelerometric signals ax, ay, az pertaining the three axes x, y z are sent in parallel to a filtering stage 110, then to a selective block generation stage 120, then to a frequency analysis stage 130, which outputs a frequency domain heart beat signal O and frequency domain accelerometric signals AX, AY, AZ pertaining the three axes x, y, z respectively.

The purpose of the filtering stage 110 is to remove the unwanted frequency bands, that is, all the bands not included in the band of interest of the heart rate. Since the band of interest of the heart rate is, for example, the interval of frequencies between 40 bpm (beats per minute) and 200 bpm, the unwanted bands include a low-frequency band (between 0 bpm and 40 bpm) and a high-frequency band (between 200 bpm and half the sampling frequency). Both the low-frequency and the high-frequency unwanted bands are removed to clear the heart signal from noise. In addition, the low-frequency unwanted band is removed because it contains a strong sub-band (between 0 bpm and a few bpm) that negatively interferes with the frequency-analysis stage. More specifically, since the frequency-analysis stage is not limited to orthogonal frequency points, but it calculates also non-orthogonal frequency points, the presence of a strong sub-band in the very low end of the spectrum would cause this sub-band to interfere with the calculation of the non-orthogonal frequency points. In addition, the high-frequency unwanted band are removed in order to facilitate prevention of aliasing, in case decimation is performed.

Each of such stages 110, 120, 130 include four banks in parallel to perform substantially the same operations respectively on the digital optical heart beat signal o and the three digital accelerometric signals ax, ay, az. Of course adjustments can be possible to take in account the different nature of the optically acquired heart signal and of the accelerometric signal. For instance the four banks of the filtering stages 110 can have the same structure, e.g., the one described with reference to FIGS. 4A and 4B. This allows to have signals at the output of the banks of the filtering stage 110 with basically the same delay and provides simplicity of implementation or design. Nevertheless, in various embodiments the filtering banks can have differences to take in account differences among the input signals.

Downstream the frequency analysis stage 130 the frequency domain heart beat signal O and the frequency domain accelerometers signals, AX, AY, AZ are fed to an estimation module 200 which includes a motion compensation block 210 and a detection block 220. The motion compensation block 210 compensates the frequency domain heart beat signal O using the values of the frequency domain accelerometers signals, AX, AY, AZ. The compensated output, O', of such motion compensation block 210, namely a compensated frequency domain heart beat signal O', is fed to the detection block 220 which computes a detected heart rate estimate d, e.g., identifies the main frequency of the compensated frequency domain heart beat signal O', which is then outputted as detected heart rate estimate d.

Such detected heart rate estimate d is fed to a correction module 400, performing a model estimation, which also receives the frequency domain accelerometers signals, AX, AY, AZ. In the correction module 400, the detected heart rate estimate d is sent as input to a decision block 410 which decides which value, between the detected heart rate estimate d and a predicted estimate m, to send as decided heart rate r. The succession of decided heart rate values r form the series of heart rate estimate values r, e.g., the output of the method described by the block diagram of FIG. 2.

Also, a non-linear prediction calculation block 300 receives the frequency domain accelerometers signals, AX, AY, AZ and calculates a predictor p. Such predictor p is fed to the correction module 400, specifically to a model learning block 430 which also receives from the decision block 410 the detected heart rate estimate d. The model learning block 430, on the basis of the predictor p and of the frequency domain accelerometers signals, AX, AY, AZ calculates linear parameters α and β, respectively the constant term and the first degree coefficient of a linear function, which are fed to a linear function calculation block 420, together with the predictor p from the non-linear prediction calculation block 300. The linear function calculation block 420 outputs the predicted estimate m on the basis of the linear function, as better detailed in the following. Thus, summarizing, a parametric model in the form of a linear function calculates a predicted estimate m of the heart rate from the predictor p and the linear parameters α and β.

As mentioned, the decision block 410 chooses which value between the detected heart rate estimate d and the predicted estimate m represents the decided heart rate r. The decision block 410 in various embodiment can simply select to send either the detected heart rate estimate d or the predicted estimate m as output. However, in an embodiment, better detailed in the following the decision block 410 performs a decision which operate in a smoothed manner, to filter out abrupt changes due to the transitions between the two estimators, the detected heart rate estimate d, which represent a first optical estimator, and the secondary predicted estimator, m, supplying as an output the decided heart rate estimate r and, ultimately, the series of heart rate estimate values r.

Figure 5:
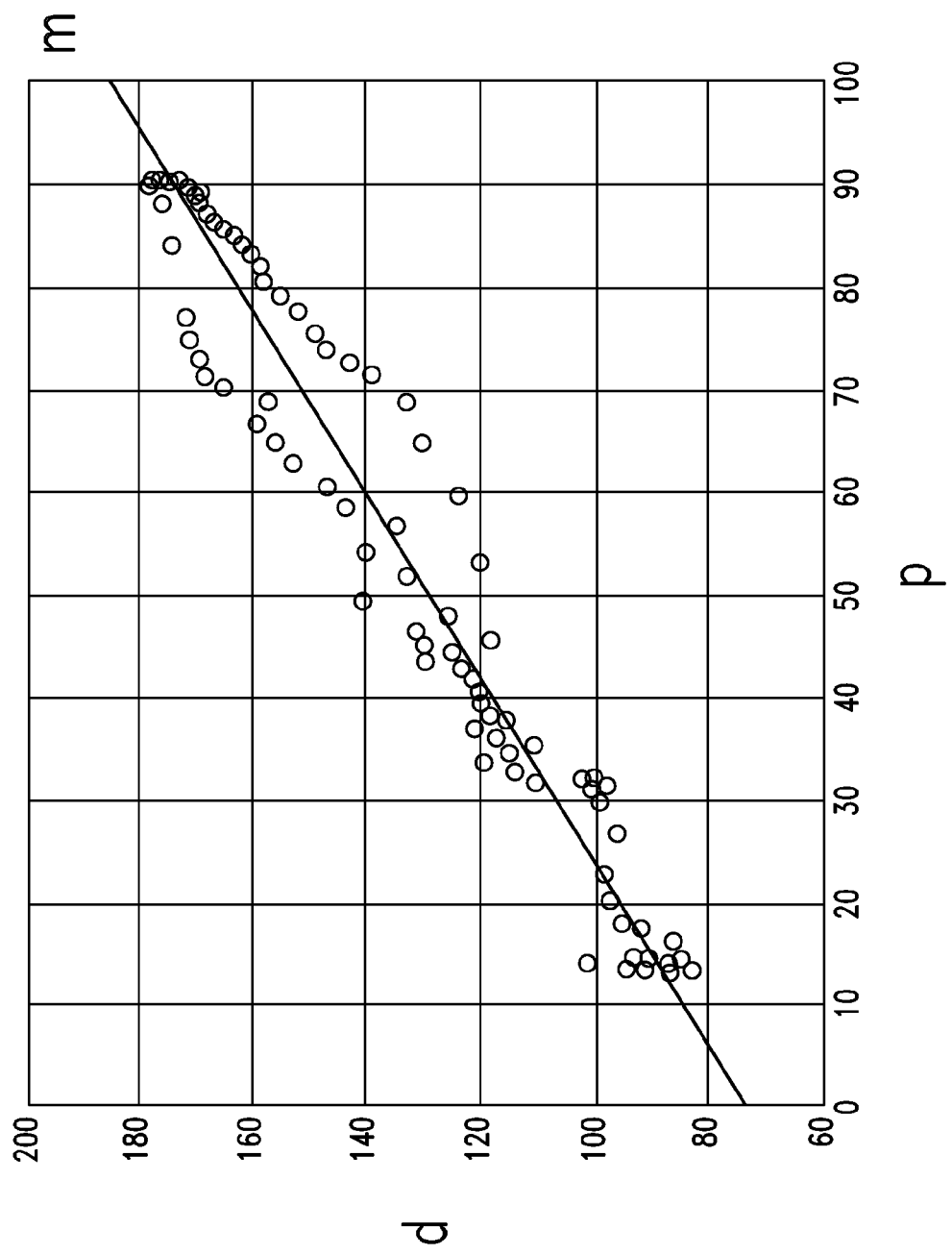
FIG. 5 shows a diagram representing an embodiment of a model applied by the method described in FIG. 2.
Figure 7:
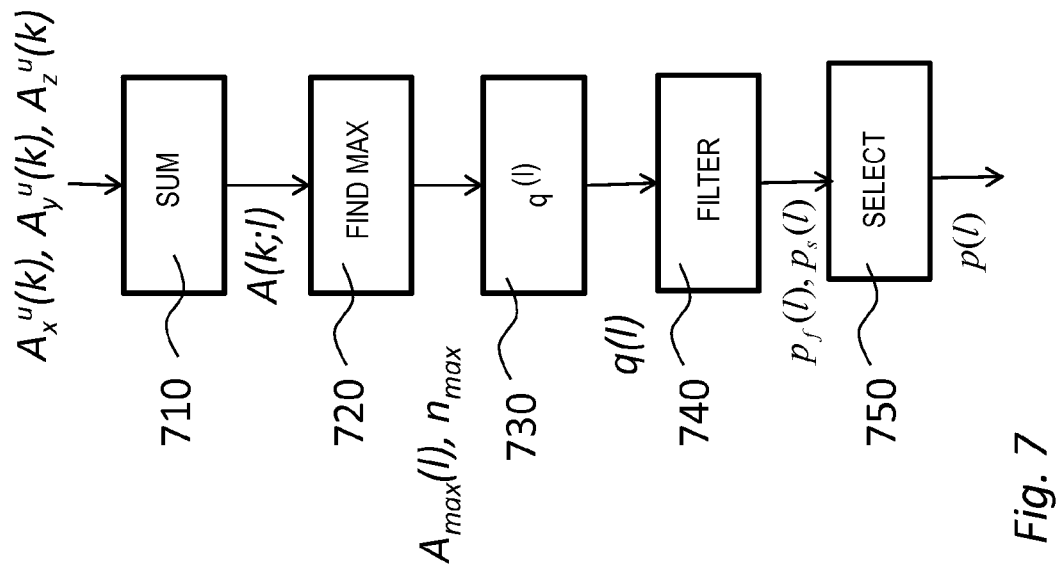
FIGS. 6, 7 and 8 represents flow diagrams detailing example operations of the method of FIG. 2.

When the decision block 410 operates its choice, if the optical estimate d is selected, such optical estimate d and the predictor p evaluated at the same time are stored, in particular in respective FIFO memories $c_x$, $c_y$, the pair of values identifying an observation point (p,d) on a predictor-estimate diagram, as better shown with reference to FIG. 5, which is used to refine the model in block 430. FIG. 5 shows a scatter plot of such observation points, (p,d), e.g., the detected heart rate d and the predictor p values. The line shown in FIG. 5 corresponds to predicted estimate m=α+β*p.

The method attempts at learning the value of linear regression parameters α and β on the basis of points (p, d). For efficiency reasons, the number of points on the basis of which the linear regression parameters α and β are maintained limited in number, since the number of the observation points (p, d) grows rapidly, one point being stored each time the decisor 410 chooses to select the estimate d. This may be obtained by a procedure which, as better detailed in the following, includes collapsing the observation points (p, d) which are sufficiently similar or near one to the other in a single point, and includes substituting with the most recent observation points the oldest observation points, using the FIFO data structures. The size of such FIFO structures is equal to the maximum number of points on the basis of which the regression line is traced. The observation points are no longer of the type of pairs (p, d), but collapsed unique elements contained in the FIFO (cx, cy).

The output of the method for the estimation of the heart-rate 1000, directed to the local display 12, the microcontroller 11 or the remote device 30, is the numerical time series of estimates r, r(ns), ns being the index of the estimate produced. For instance a decided estimate r is produced every three seconds, so that the index ns is increased every three seconds. The method for the estimation of the heart-rate 1000 makes an attempt to update such series r, with a tentative update period of the estimate $T_e$, e.g., every $T_e$ seconds from the last estimate, for example $T_e$=5 s or $T_e$=1 s. Occasionally the updating attempt fails, due to poor signal conditions; in this case the subsequent update may be provided after a period longer than the update period $T_e$.

With reference to the operations shown in FIG. 2, in various embodiments such method not necessarily includes all the operations and modules shown in such FIG. 2 and describe above, or, alternatively, some of the operations and module can be different.

By way of example, in various embodiments, the method for the estimation of the heart-rate using photoplethysmography on a body organ, in particular on a wrist of a user, comprises acquiring optically from sensor 13a, 13b, 17 from said body organ a heart beat signal o, acquiring from sensor 21 an acceleration signal ax, ay, az representative of the acceleration of said body organ, selecting by the stage 120 data blocks $B_o$, $B_x$, $B_y$, $B_z$ of said acquired heart beat signal o and acceleration signal ax, ay, az, compensating in block 210 said heart beat signal o by the acceleration signal ax, ay, az, calculating in block 210, 220 a heart-rate value, the heart rate estimate d on the basis of the resulting compensated heart beat signal O', the compensation operation 210, 220 including obtaining in stage 130 from said selected data blocks Bo, Bx, By, Bz corresponding frequency domain data blocks for the heart rate signal O and for the acceleration signal AX, AY, AZ, performing a motion compensation 210 of the frequency domain data blocks for the heart beat O using the frequency domain data blocks for the acceleration signal AX, AY, AZ.

In various embodiments, the correction module 400 operates on the basis of the heart rate estimate d and of the predictor p originated by the non linear prediction calculation block 300 to produce the decided heart rate value r.

Figure 8:
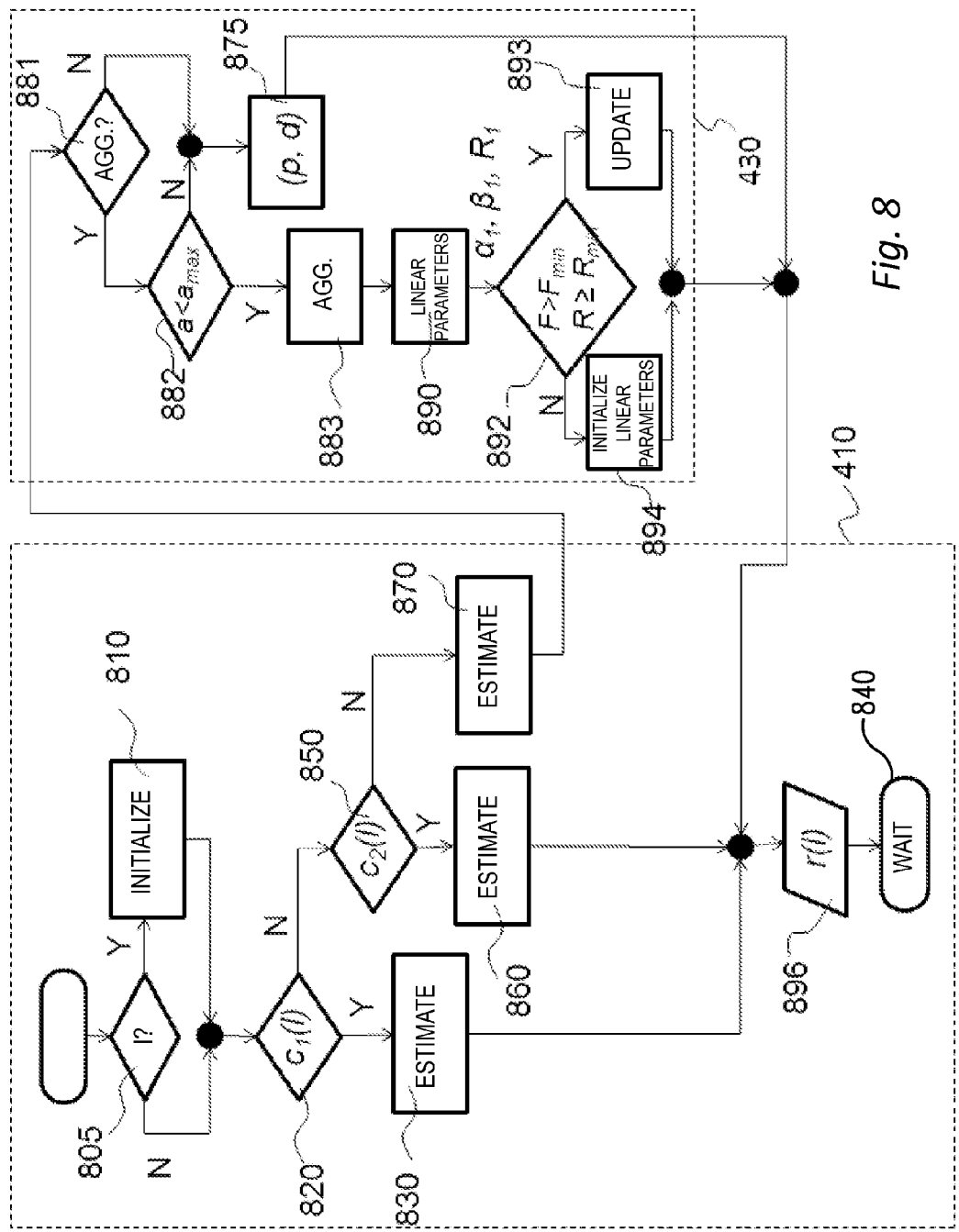

In various embodiments the decided heart rate value r is calculated by a smoothed decision operation (as detailed in FIG. 8).

Figure 3:
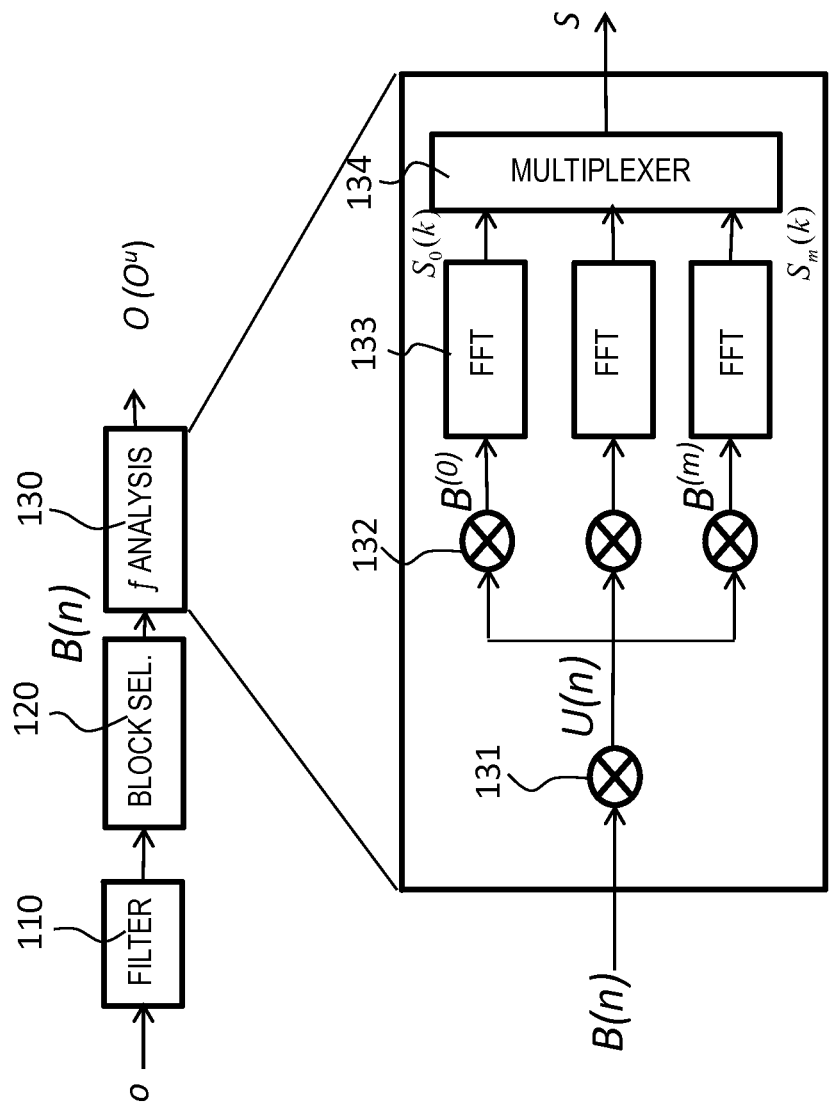
FIG. 3 represents a diagram detailing an operation of the method described in FIG. 2.

Now the operation of the specific blocks and stages shown in FIG. 3 will be detailed.

Figure 4A:
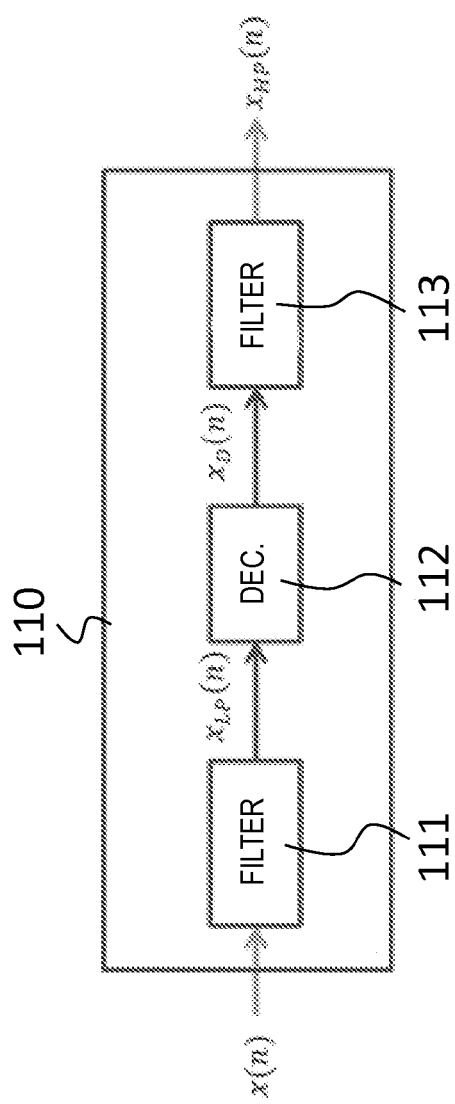
FIGS. 4A and 4B detail a filtering operation of the method described in FIG. 2.

As regards the banks of the filtering stage 110, each comprises a low-pass FIR (Finite Impulse Response) filter 111, as shown in FIG. 4A, followed by a high-pass filter 113. Between the low-pass filter 111 and the high pass filter 113 a factor-2 decimation stage 112 is optionally applied, as in the example shown, in order to reduce the memory footprint of the algorithm. The filters are independently applied to each of the four input signals: the optical sequence of values corresponding to the optical signal o, o(n), n being as mentioned the numeric index of the samples acquired, and analogously the three accelerometric sequences ax(n), ay(n) and az(n), corresponding to signals ax, ay and az. The filters of filtering stage 110 produce respectively four filtered time domain signals, one, $o_{HP}(n)$, pertaining the optical sensor 17, and the other three pertaining each axis of the accelerometric sensor 21, $ax_{HP}(n)$, $ay_{HP}(n)$, $az_{HP}(n)$ respectively.

Figure 4B:
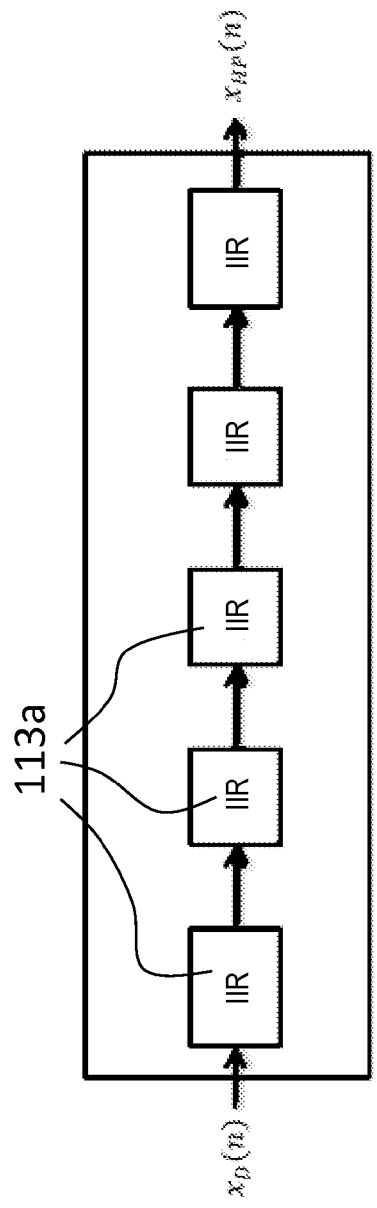

Since the required transfer function of the high-pass filter 113 is very stringent, the high pass filter 113 may be implemented by means of a chain of five IIR (Infinite Impulse Response) filters 113a, as illustrated in FIG. 4B.

Each of the five IIR filters 113a have the following transfer function:

$$H(z) = \frac{b_0 + b_1 \cdot z^{-1} + b_2 \cdot z^{-2}}{1 + a_1 \cdot z^{-1} + a_2 \cdot z^{-2}}$$

where
$a_1 = -1.905850154697027$
$a_2 = 0.911145313595591$
$b_0 = 0.979650817189758$
$b_1 = -1.907660496005129$
$b_2 = 0.929684155087730$ The transfer function resulting from the cascade of the five IIR filters accomplishes the removal of the unwanted low-frequency band as explained before, especially the very first portion of the unwanted low-frequency band.

For what regards the selection block generation stage 120, this stage comprises four parallel banks receiving as input each a respective sequence corresponding to one of the four filtered time domain signals coming from the sensors, $o_{HP}(n)$, $ax_{HP}(n)$, $ay_{HP}(n)$, $az_{HP}(n)$, and generating four time domain data blocks by operating on such respective filtered optical and accelerometric sequences. The four generated time-domain data blocks, $B_o$ from the data in the optical sequence $o_{HP}(n)$, and $B_x$, $B_y$, $B_z$ from the data in the accelerometric sequences $ax_{HP}(n)$, $ay_{HP}(n)$, $az_{HP}(n)$, are time synchronized, which means that the first samples in each bank of the stage 120 are time aligned to the same temporal reference, which marks the beginning of the time domain data blocks. The selection of the time domain data block may be done by means of a procedure, e.g., the selective block-generation better detailed below, that repeatedly tests the data blocks tentatively constructed on the time domain optical sequence o(n) until a given condition is met. The procedure provisionally generates a data block from the optical sequence o(n), testing the condition, and, in case the condition is met, exiting the procedure and forwarding that block $B_o$ to the next stage of the method (along with the three time-aligned accelerometric data blocks $B_x$, $B_y$, $B_z$), while, in case it is not met, generating a new provisional block that is time shifted relative to the previous block. In this way, the new provisional block contains a sub-block with more recent samples relative to the previous block.

Figure 6:
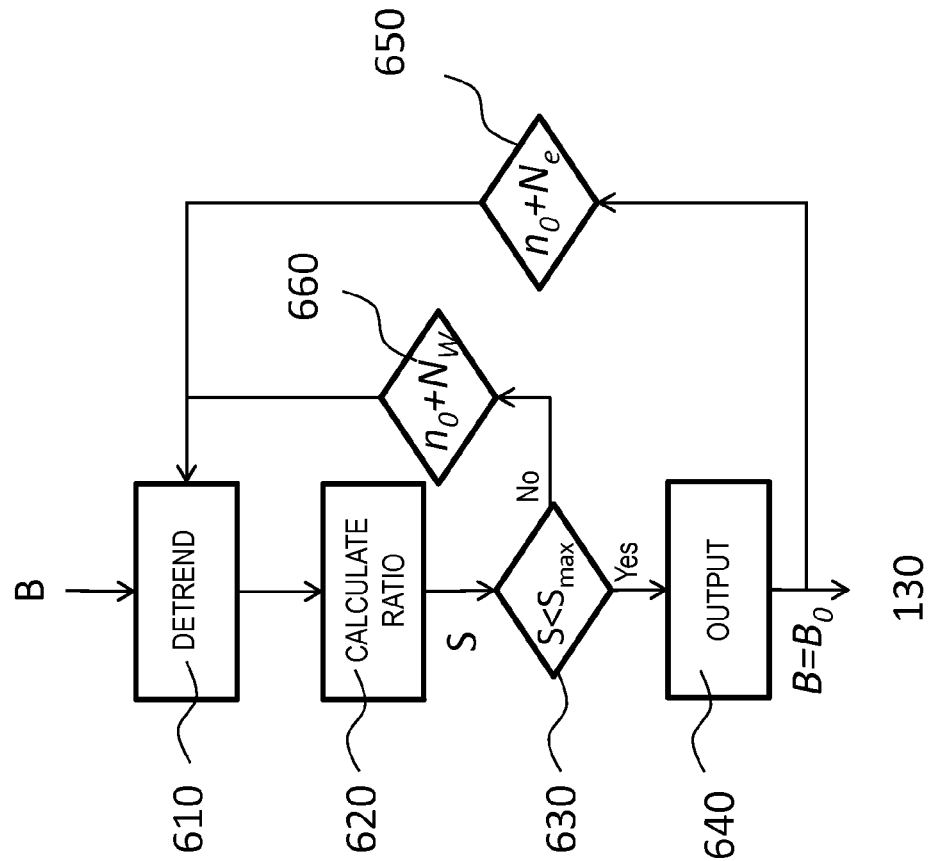

In an embodiment, the selective block generation procedure operates as follows and as detailed in FIG. 6, where $n_0$ indicates an index of the most recent optical sample of the optical sequence o(n) stored in memory out of the filtering stage 110 and 8 indicates a data block formed from the N most recent optical samples, from $n_0$ backwards:

a de-trending step 610 is first operated on the block B. A block is said to be de-trended if its samples are replaced with the result of the subtraction of the mean value of its original samples from each original sample. In this way, the mean of the samples of the de-trended block equals zero;

then in a step 620 it is calculated a ratio S on the de-trended block B as the maximum value of B over the mean of the de-trended data block B. N is the number of samples in the block.

$$S = \frac{\max_{n=0 \ldots N-1} |B(n)|}{\text{mean}|B(n)|}$$

if in a step 630 test condition is evaluated that such ratio S is lower than a determined threshold value $S_{max}$:

in a step 640 the stage 120 gives as output the optical data block $B_0$, set equal to block B, and the three time-aligned and de-trended accelerometric blocks $B_x$, $B_y$, $B_z$, which are forwarded to the frequency-analysis stage 130;

it is then waited in a step 650 until the filtering stage 110 outputs the sample $n_0 + N_e$ and repeated the above procedure starting from the de-trending step 610 to generate the next blocks;

else, if the condition 630 is not met, in a step 660 it is waited until the filtering stage 110 outputs the sample $n_0 + N_w$ (the new most recent optical sample) and then it is repeated the procedure from the de-trending step 610, thus generating a new provisional block that is time shifted relative to the previous block.

The parameter N indicating the number of most recent optical samples taken into account is set to 1024, but other values are also possible (although with some effects on performance and memory requirements).

The throughput parameter $N_e$ may be set according to the desired throughput of heart-rate estimates, e.g., update period, $T_e$:

$$N_e = T_e \cdot \frac{f_s}{2}$$

The factor 2 in the denominator of the previous formula refers to the case of the sampling-rate reduction through decimation.

For example, in case a throughput of 0.2 Hz is required (one estimate every 5 s), and the sample frequency $f_s$ is 100 Hz, the throughput parameter $N_e$ is set to 250 samples. The value of the parameter $N_w$ can be set to any amount smaller than throughput parameter $N_e$, for example to 50 samples.

For what regards the frequency analysis stage 130, this stage operates independently on each of the four blocks $B_o$, $B_x$, $B_y$, $B_z$ at the output of the selective block generation stage 120. The four time domain data blocks $B_o$, $B_x$, $B_y$, $B_z$ pass through the same type of processing. Each of the four time domain data blocks $B_o$, $B_x$, $B_y$, $B_z$ is transformed into the frequency domain in the form of a number K of frequency lines, or frequency bins. The K bins are obtained by interleaving a number M of N-point FFTs (Fast Fourier Transform) as shown in reference to FIG. 3. In this way a higher (better) frequency resolution can be obtained, as compared to a single FFT. Not all of the N points are necessary for each FFT, but only a subset of K/M points, as described next. K it is assumed to be an integer multiple of M. Each of the M FFTs are calculated respectively on blocks $B^{(m)}$, with m=0 ... M−1 obtained by multiplying in a multiplier block 132 the samples of the block U(n) by a complex-valued sequence:

$$B^{(m)}(n) = U(n)e^{\frac{j2\pi n \Delta m}{f_s}}$$

where m=0 ... M−1, n=0 ... N−1 and U(n) is obtained by multiplying in a multiplier block 131 the samples of the generic block B(n) by an apodization function (or window function), for example a Taylor function. The use of apodization functions is well known in the prior art and has the purpose to attenuate the artifacts due to the secondary lobes introduced by the operation of block selection.

The complex argument of the exponential includes the product of index m identifying the m-th FFT, index n identifying the sample and a frequency resolution of the frequency analysis $\Delta$, over the sampling frequency $f_s$.

The m-th FFT, calculated in block 133 on the block $B^{(m)}$ is denoted with $F_m(k)$, while $S_m(k)$, indicates the squared modulus of the m-th FFT: $S_m(k)=|F_m(k)|^2$, also calculated in block 133.

The output of the frequency analysis 130 is a block S of frequency domain values, formed with such squared modulus of the FFT $S_m(k)$ by a multiplexer 134 as follows:

$$S = \{S_0(k_0), \ldots, S_{M-1}(k_0), S_0(k_0+1), \ldots,$$
$$S_{M-1}(k_0+1), \ldots, S_0\left(k_0+\frac{K}{M}-1\right), \ldots, S_{M-1}\left(k_0+\frac{K}{M}-1\right)\}$$

where $k_0$ is the index corresponding to the lower bound of the frequency band of interest, as described later.

The K elements of S are numbered from 0 to K−1 so that:

$$S(v)=S_m(k_0+q)$$

where v=qM+m, with q and m univocally determined by the conditions: m<M, q integer, and m integer.

Each element S(v) corresponds therefore to the frequency $(k_0+q)\cdot M\cdot\Delta+m\cdot\Delta$, where the quantity $\Delta$ is the frequency resolution: $\Delta=1/(M*D)$, and D is the duration in seconds of the analysis block. By way of example, if D=20.48 s, and M=3, then $\Delta=0.0162$ In order to determine the value of K, that is the number of elements in the set s, it is possible to proceed in the following way. First, a band of frequencies of interest is specified, for example the band 40 bpm-200 bpm. Secondly, the index $k_0$, is determined by imposing $$S(0) < \frac{40}{60},$$

which leads to $$k_0 \cdot M \cdot \Delta < \frac{40}{60},$$

and solving with respect to $k_0$, it is obtained $k_0=13$.

Finally, it is imposed $$S(K-1) > \frac{200}{60},$$

and solving it is obtained K=168.

Finally the block S is normalized. Within the context of the present description, the normalization of a block X containing K elements produces the block $X^u$ defined as follows:

$$X^u(k) = \frac{X(k)}{S}, k = 0, \ldots, K-1$$

$$\text{where } S = \sum_{k=0}^{K-1} X(k)$$

The normalized block S is thus indicated by $S^u$.

A normalized block $S^u$ is constructed on each of the four time domain data blocks $B_o$, $B_x$, $B_y$, $B_z$, and these normalized blocks, which are frequency domain data values, are denoted respectively with $O^u$, $A_x^u$, $A_y^u$, $A_z^u$.

For what regards the motion compensation 210, this operation consists in calculating a motion compensated block $O^{MC}$ defined as follows:

$$O^{MC}(k)=O^u(k)-[v_X\cdot A_X^u(k)+v_Y\cdot A_Y^u(k)+v_Z\cdot A_Z^u(k)],$$
$$k=0,\ldots,K-1$$

Where $v_X$, $v_Y$, $v_Y$ are three scalar weight values, for example set to 1; $O^u(k)$, $A_x^u(k)$, $A_y^u(k)$, $A_z^u(k)$ are the normalized frequency domain data block outputted by the frequency analysis stage 130 respectively for the optical and the three accelerometric sequences.

The derivation of the motion-compensation formula can be made proceeding in the following way.

The signal $O^u(k)$ can be decomposed into five contributions: a heart-beat signal $O_h(k)$ (the wanted signal), three motion-induced artifact signals, $O_x(k)$, $O_y(k)$, and $O_z(k)$, and a non-motion-induced noise $O_n(k)$. So it is possible to write:

$$O^u(k)=O_h(k)+O_x(k)+O_y(k)+O_z(k)+O_n(k)$$

The artifact components, being caused by motion, can be written in terms of transfer function of the accelerometric input:

$$O_X(k)=V_X(k) \cdot A_X^u(k)$$

$$O_Y(k)=V_Y(k) \cdot A_Y^u(k)$$

$$O_Z(k)=V_Z(k) \cdot A_Z^u(k)$$

where $V_X(k)$, $v_Y(k)$, and $V_Z(k)$ are three transfer functions defined as:

$$V_X(k) = \frac{O_X(k)}{A_X^u(k)}$$

$$V_Y(k) = \frac{O_Y(k)}{A_Y^u(k)}$$

$$V_Z(k) = \frac{O_Z(k)}{A_Z^u(k)}$$

Perfect motion compensation would require the knowledge of the three transfer functions. Unfortunately, the transfer functions may be unknown for the following reasons:
 they are time variant;
 they are motion dependent;
 a model for their estimation is not available and it is not easy to derive;
 they are subject dependent.

For the reasons listed above, the transfer functions have been approximated to a constant value both in the time and in the frequency axis, denoted respectively with $v_X$, $v_Y$, and $v_Z$. Despite this approximation, the performance of the motion compensation stage is still acceptable in that the purpose of motion compensation is not the complete (over the whole frequency band) estimation of $O_h(k)$, but, rather, is the estimation of only the position of the dominant frequency component of $O_h(k)$, as it will be described next. The optimal values for the three constant (approximated) transfer functions can be obtained, for example, through an optimization process that maximizes the performance of the final heart-rate estimation with respect to $v_X$, $v_Y$, and $v_Z$. The values $V_X=1$, $v_Y=1$, and $v_Z=1$ offer a first guess of the optimal solution.

Another aspect of the motion compensation stage of an embodiment is the operation of normalization applied to the four signals (one heart signal and three accelerometric signals). The result of this operation is to equalize the energy of the four signals to the unitary value. This operation brings the magnitude of the spectra of the four signals to the same range of values. Failure to do this might cause the subtraction operation to be not effective, in that it would be performed on terms of non-comparable magnitudes. Through the operation of normalization, a strong frequency component present in the spectra of any of the accelerometric signals can effectively cancel the corresponding artifact on the optical signal.

Thus, the motion compensation substantially includes subtracting from the frequency domain optical signal, $O^u$, e.g., the heart beat signal in the frequency domain, a linear combination of the three frequency domain acceleration signals $A_x^u(k)$, $A_y^u(k)$, $A_z^u(k)$ multiplied by a respective scalar weight $v_X$, $v_Y$, $v_Y$.

For what regards the detection operation 220, the detection includes finding an argument $k_{max}$ of the maximum value of the motion compensated block $O^{MC}(k)$:

$$k_{max} = \underset{k}{\operatorname{argmax}}(O^{MC}(k))$$

The frequency bin $k_{det}$ of the detected heart-rate d can then be obtained from such argument $k_{max}$ as the sum of the index of the first useful bin $k_0$ and argument $k_{max}$:

$$k_{det}=k_0+k_{max}$$

Optionally, the estimate of the frequency bin $k_{det}$ can be refined by a 3-point interpolation:

$$k_{det}=k_{det}+f_{int}(O^{MC}(k_{max}-1),O^{MC}(k_{max}),O^{MC}(kmax+1))$$

where $f_{int}(y_1,y_2,y_3)$ is any interpolation function such that:

$$f_{int}(y_1, y_2, y_3) = \begin{cases} \in (-1, 0) & \text{if } y_1 > y_3 \\ 0 & \text{if } y_1 = y_3 \\ \in (0, 1) & \text{if } y_1 < y_3 \end{cases}$$

Finally, the detected heart rate estimate d is obtained by performing a rescaling the frequency bin $k_{det}$ of the detected heart-rate d:

$$d=60 \cdot \Delta \cdot k_{det}$$

For what regards the predictor calculation in block 300, the frequency analysis stage 130 produces a set of four frequency-domain data blocks at output times $t_l=t_{l-1}+\tau_l$, where $\tau_l$ is the interval between two consecutive calculations and l is the index of the output times. This interval $\tau_l$ is usually equal to the update period $T_e$, but it can be longer in case the selective block-generation stage 120 enters in the step 660 of the selective block generation procedure in which it is waited until the filtering stage 110 outputs the sample $n_0+N_W$. The l-th set of four frequency domain blocks, calculated at time $t_l$ is denoted as $O^u(n; l)$, $A_X^u(n; l)$, $A_Y^u(n; l)$, and $A_Z^u(n; l)$.

The calculation of the predictor in block 300 comprising the following steps:
 a step 710 of summing the normalized frequency domain blocks of the three accelerometric signals to obtain a sum of accelerations $A(k;l)$ $$A(k;l)l)=A_X^u(k;l)+A_Y^u(k;l)+A_Z^u(k,l)$$

a step 720 of finding the maximum $A_{max}(l)$ of the sum of accelerations $A(k;l)$ and the corresponding argument $n_{max}$:

$$A_{max}(l) = \max_k A(k; l)$$

$$n_{max}(l) = \underset{k}{\operatorname{argmax}} A(k; l)$$

a step 730 of calculating a time sequence q(l) as function of the maximum $A_{max}(l)$ of the sum of accelerations $A(k;l)$ and of the corresponding argument $n_{max}$ as follows:

$$q(l)=0.1 \cdot (60 \neq \Delta \neq (k_0+n_{max}(l))+10 \cdot \text{Log}(A_{max}(l)))$$

a step 740 of filtering the time sequence q(l) by means of two first-order IIR filters as follows:

$$p_f(l)=\alpha_f(l)\cdot p_f(l)+(1-\alpha_f(l))\cdot q(l)$$

$$p_s(l)=\alpha_s(l)\cdot p_s(l)+(1-\alpha_s(l))\cdot q(l)$$

where:

$$\alpha_f(l)=0.99^{5-\tau_l}$$

$$\alpha_s(l)=0.998^{5-\tau_l}$$

a step 750 of selecting as predictor at time $t_l$, p(l), the maximum between the first filtered sequence $p_f(l)$ and the second filtered sequence $p_s(l)$:

$$p(l)=\max(p_f(l),p_s(l))$$

The previous formula represents the fact that the predictor p(l) is constructed as the maximum between two intermediate functions, $p_f(l)$ and $p_s(l)$. These two intermediate functions are two filtered versions of the time series of q(l). If to the time sequence q(l) is given the interpretation of the level of physical exertion of the user, the two filtered output of the time sequence q(l) represent two different responses to physical exertion. In particular, the series $p_f(l)$ represents a fast response to the time sequence q(l), while $p_s(l)$ represents a slow response to the time sequence q(l). Through the operation of maximum search max, the series $p_s(l)$ becomes relevant during periods of physical recovery (that is when the level of physical exertion is decreasing), while the series $p_f(l)$ becomes relevant during periods of increasing physical activity. This is consistent with the fact that cardiac output (and therefore cardiac frequency) responds differently to increases and decreases of physical activity. Typically, heart rate responds quickly to an increase of physical activity, and responds much more slowly to a decrease of physical activity.

For what concerns the correction stage 400, this stage uses the values of the predictor p(l) and of the detected heart rate estimate d(l) to arrive at a heart-rate estimate r(l).

The correction procedure 400 includes the following steps:

a step 805 in which is verified if an initialization of values is required. This occurs usually only at the power-on of the system. In the affirmative (Y), a step 810 of initialization of the values is performed. Values are by way of example initialized as follows:

I=1
$\alpha=\alpha_0$
$\beta=\beta_0$

In the following for simplicity of representation index I will be used instead of time $t_l$.

Three FIFO memories, $c_X$, $c_Y$, which store, as mentioned, the observation points (p,d) each time the estimate d is selected, and a weight computation FIFO $c_W$ which is used in the aggregation of the points. FIFO memories $c_X$, $c_Y$, $c_W$ as described in the following, are initialized as empty. In particular, the predictor FIFO memory $c_x$ sequentially stores the values of the predictor p at each time instant l at which the estimate d is selected.

The estimate FIFO memory $c_y$ sequentially stores the values of the estimate d at each time instant l.

The weight FIFO memory $c_w$ increments the values of a weight factor at each time instant l.

$\alpha_0$ and $\beta_0$ are initial guesses set for the first order term and for the constant term of the linear regression, for example, $\alpha_0=80$ and $\beta_0=0.8$. Other values are suitable, although they have an effect on the accuracy of the final heart rate estimate;

after step 810 or if the condition verified at step 805 is negative (N), e.g., initialization has been already performed a step of evaluation 820 of a condition $c_1(l)$ at time I is performed:

$$c_1(l)=(d(l)<d_{min}(l)) \text{ or } (d(l)>d_{max}(l))$$

where:

$$d_{min}(l)=m(l)-G$$

$$d_{max}(l)=m(l)+G$$

$$m(l)=\alpha+\beta\cdot p(l)$$

G indicates a safety margin set for instance to 40, therefore $d_{min}$ and $d_{min}$ represents two lines parallel to m(l) which identify the lower and upper limit of a safety range. If the value estimate d is outside such range is considered not a good value.

If the condition $c_1(l)$ is true then the estimate r(l) is, in block 830:

$$r(l) = \frac{r(l-1) + m(l)}{2}$$

The correction is finished, and the procedure wait in a step 840 for the next iteration, updating the time index I, thus it is I=I+1 and going back to operation 820.

Else if condition $c_1(l)$ is false, the condition $c_2(l)$ is evaluated at time I in a step 850:

$$c_2(l)=(d(l)-d(I-1)<g_1) \text{ or } (d(l)-d(I-1)>g_2) \text{ and not } c_1(I-1)$$

$g_1$ and $g_2$ are parameters set for instance to $g_1=-10$ and $g_2=20$ which set a confidence range [g1, g2] for the variation between time adjacent estimates. If the estimates d(l) are within said range, $c_2(l)$ is false, meaning that the estimate d is reliable and can be selected as valid output (see step 870 below).

Other values are possible, although they may affect the accuracy of the heart rate estimates.

If condition $c_2(l)$ is true, the final estimate r(l) is evaluated in a step 860 as the median of the latest three detected estimates d(I−2), d(I−1),d(l):

$$r(l)=\text{median}(d(I-2),d(I-1),d(l))$$

It is noted that if $c_2(l)$ is true the optical estimate d is considered in any case at least partly reliable, since it is used to obtain the final estimate r(l), although through the median function. If $c_2(l)$ is false, the reliability of the optical estimate d(l) is greater, thus there is no need of taking in account the two previous estimates d(I−1), d(I−2) and the estimate d(l) is sent directly as output r(l). Thus operation 860, within the decision operation performed by block 410, represents a smoothing operation applied taking in account a plurality of estimates d at different times, such as I−2, . . . , I and averaging over them.

Also in this case the correction procedure is finished and the procedure waits in a step 840 for the next iteration, updating the time index I, thus it is I=I+1 and going back to operation 820.

If condition $c_2(l)$ is false, the final estimate is set in a step 870 to the detected estimate d(l):

$$r(l)=d(l)$$

In FIG. 8 steps 810-894 are indicated by a dashed polygonal as operated by the decision block 410. As mentioned, the decision block 410 in its simpler form decides if the final estimate r(l) is equal to the optical estimate d(l) or to the predicted estimate m(l) on the basis of a given condition, such as $c_1(l)$ or $c_2(l)$, which evaluates if the optical estimate value is reliable. In the embodiment of FIG. 8, however, a smoothed decision is implemented, e.g., the final estimate r(l) is at least in some cases the result of an average of the current estimate with previous estimates, optical estimate d and or predicted estimate m. Specifically, while step 870 output simply the optical estimate d(l) as final estimate r(l), step 860 outputs an average over previous optical estimates, step 830 outputs an average with the previous final estimate r(l). It is clear that in various embodiments other choices of reliability conditions such as $c_1(l)$ or $c_2(l)$ and other type of averaging are possible to the person skilled in the art.

The result of step 830, 860 or 870 are collected in a block 896 which supplies the final estimate r(l) outputted by the decision block 410.

Preferably, the update of the linear block 430 includes performing an aggregation operation, described here below, to keep low the number of observation points in the FIFO. Thus, in FIG. 8 it is indicated, after step 870, a step 881 of evaluating if aggregation is required. In the negative, after the step 870, since the decision block 410 has chosen the detected estimate d(l), the linear model in block 430 is updated, this meaning that observation point (p, d) are stored in a step 875 in the FIFO $c_x$, $c_y$. Then step 896 is performed, outputting the final estimate r(l).

If step 881 indicates that an aggregation procedure is to be performed, it is executed a step 882 of finding an element a in the predictor FIFO $c_x$, storing a time sequence of predictors p, closest to the predictor p(l):

$$a = \min_k |p(l) - c_x(k)|$$

and evaluating if $\alpha < \alpha_{max}$, e.g., the closest element a in the predictor FIFO $c_x$ is closer than a threshold value to the predictor p at time l. This corresponds to evaluate if the new observation point is near to an existing point stored in the FIFO.

In the affirmative in a step 883 it is set:

$$j_0 = \arg\min_j |p(l) - c_x(j)|$$

$$w = \max(0.2, 1 - 0.1 \cdot c_w(j_0))$$

$$c_x(j_0) = c_x(j_0) + w \cdot (p(l) - c_x(j_0))$$

$$c_y(j_0) = c_y(j_0) + w \cdot (d(l) - c_y(j_0))$$

$$c_w(j_0) = c_w(j_0) + 1$$

$j_0$ is a parameter indicating the value of index j of the value $c_x(j)$ in the predictor FIFO $c_x$ which minimizes the distance with the predictor p(l) at time index l, which identifies an aggregating point $(c_x(j_0), c_y(j_0))$.

$c_w$ is in general a weight factor FIFO. $c_w(j_0)$ represents a weight factor of the aggregating point $(c_x(j_0), c_y(j_0))$, e.g., a FIFO counter which is incremented by one at each aggregation of a new observation point (p,d) to such aggregating point$(c_x(j_0), c_y(j_0))$.

The operation of aggregation or collapse in a single point is a weighted average performed on both the values in the predictor FIFO $c_x$ and in the estimate FIFO $c_y$. The aggregating points $(c_x(j_0), c_y(j_0))$ with the greater weight are those which are the results of a greater number of aggregations in the past. The weight of the aggregating point is used to establish a weight of the newly aggregated point (p,d), which is represented by w. Thus, the relations above implements the operations of assigning to the new point or aggregated (p, d) a relative weight which is inversely proportional to the weight of the aggregating point $(c_x(j_0), c_y(j_0))$ to which is aggregated.

In this way, if the aggregating point $(c_x(j_0), c_y(j_0))$ is reliable, the aggregated point (p,d) has not to change significantly its value.

Else if condition 882 is not met, it is performed a push operation on the content of the FIFO, before passing to step 875.

$$c_x = \mathrm{push}(p(l), c_x)$$

$$c_y = \mathrm{push}(d(l), c_y)$$

$$c_w = \mathrm{push}(d(l), c_w)$$

The function push(val, list) first shifts one position rightwards all the elements contained in the list (in this way discarding the rightmost element) and then inserts the number val at the leftmost position of the list.

Then in a step 890, following step 883, are calculated the linear regression parameters $\alpha_1$, $\beta_1$, $R_1$ of the set of points $\{(c_x(j), c_y(j))\}$, for j=0, . . . , F(l)−1, F(l) being the number of elements in the FIFO memory at time index l.

R indicates the coefficient of determination computed in the classical mode from the linear regression (it is $R^2$ properly, R for short). The coefficient of determination R measures the amount of linearity of the aggregated points, which are used as reliability indication. R1 indicates therefore the coefficient of determination computed over the current aggregated points, e.g., the points $(c_x, c_y)$ in the FIFO structures, while $R_{min}$ indicates a minimum threshold level above which the linear model is considered as reliable.

In a step 892 it is evaluated if the number of elements in the FIFO F(l) is at least a minimum value $F_{min}$ and if the coefficient of determination R is greater equal than a minimum value $R_{min}$.

In the affirmative, in a step 893 the linear parameters are updated, setting them to the linear regression parameters $\alpha_1$, $\beta_1$ calculated in the step 890:

$\alpha \rightarrow \alpha_1$
$\beta \rightarrow \beta_1$

Else, in a step 894 the linear parameters are set to the initial values of initialization step 810:

$\alpha \rightarrow \alpha_0$
$\beta \rightarrow \beta_0$

The procedure goes to step 840 and then to step 820 to wait for the next iteration.

The parameters $F_{min}$ and $R_{min}$ are set, for example to $F_{min}$=5 and $R_{min}$=0.5. Other values are possible but performance may vary.

Steps 890-894 are indicated by a dashed square as operated by the model learning block 430 to update the linear regression parameters on the basis of the observation points storing step 875. As indicated steps 880-894 represents an accessory aggregation procedure. In various embodiments it is also possible to proceed from the observation points storing step 875 directly to linear parameters calculation step 890.

The method according to an embodiment here described facilitates overcoming noise by means of high processing gain (for instance, with 1024 points FEET is obtained a 30 dB gain).

The method according to an embodiment here described facilitates overcoming interference due to motion of the body organ in the frequency domain (motion compensation).

The method according to an embodiment here described builds a secondary estimator, e.g., a prediction, which may be used whenever the primary estimator derived by the optical signal fails.

The methods here described can be used in system and device for the continuous monitoring of the heart-rate for fitness/wellness applications. These systems and devices can be for instance wrist-wearable devices for runners monitoring their workout session. These devices can be wristwear or also earwear, smart-watches, smart-headphones.

Some embodiments may take the form of or include computer program products. For example, according to one embodiment there is provided a computer readable medium including a computer program adapted to perform one or more of the methods or functions described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some of the systems and/or modules and/or circuits and/or blocks may be implemented or provided in other manners, such as at least partially in firmware and/or hardware, including, but not limited to, one or more application-specific integrated circuits (ASICs), digital signal processors, discrete circuitry, logic gates, standard integrated circuits, state machines, look-up tables, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
    selecting heart-beat data blocks based on a received heart-beat signal;
    selecting acceleration data blocks based on one or more received acceleration signals;
    converting the selected heart-beat data blocks to heart-beat frequency domain data blocks;
    converting the selected acceleration data blocks to acceleration frequency domain data blocks;
    performing motion compensation in the frequency domain based on the converted frequency domain data blocks;
    generating an estimated heart rate based on the motion compensation;
    generating a predicted estimate based on the acceleration frequency domain data blocks; and
    generating a heart-rate signal based on the estimated heart rate and the predicted estimate, wherein a linear function is used to generate the predicted estimate, and the linear function is updated based on the generated heart-rate signal.

2. The method of claim 1, comprising generating the received heart-beat signal using photoplethysmography on a wrist.

3. The method of claim 1 wherein said motion compensation includes:
    multiplying the acceleration frequency domain data blocks by respective scalar weights; and
    subtracting the weighted acceleration frequency domain data blocks from the heart-beat frequency domain data blocks.

4. The method of claim 1, comprising:
    generating a compensated heart-beat signal; and
    generating the estimated heart rate based on the compensated heart-beat signal.

5. The method of claim 4, comprising:
    computing a non-linear predictor value based on the acceleration frequency domain data blocks; and
    generating the predicted estimate as a linear function of the predictor value.

6. The method of claim 5 wherein the generating the heart-rate signal comprises selecting one of the estimated heart rate and the predicted estimate.

7. The method of claim 5, comprising:
    averaging a plurality of estimated heart rates estimated at different times.

8. The method of claim 6, comprising:
    updating said linear function by storing a current estimated heart rate and predictor value when the estimated heart rate is selected, obtaining a sequence of observation points; and
    calculating the linear function as a regression over said sequence of observation points.

9. The method of claim 5, comprising performing an aggregation operation over said sequence of observation points.

10. The method of claim 1, comprising:
    filtering the received heart-beat signal and selecting the heart-beat data blocks based on the filtered heart-beat signal;
    filtering the received one or more acceleration signals and selecting the acceleration data blocks based on the filtered one or more acceleration signals, the filtering including low-pass filtering and high-pass filtering, the high-pass filtering using a chain of infinite impulse response filters.

11. The method of claim 1, comprising:
    generating a data block based on the received heart-beat signal;
    determining whether the generated data block satisfies a testing condition;
    when the generated data block satisfies the testing condition, converting the generated data block and data blocks based on the received one or more acceleration signals which are time-aligned with said generated data block to frequency domain data blocks; and
    when the generated data block does not satisfy the testing condition, discarding the generated data block and generating a new data block that is time-shifted relative to the previously generated data block.

12. The method of claim 4 wherein the estimating the heart rate comprises identifying a frequency of the compensated heart-beat signal.

13. The method of claim 1, comprising:
interleaving a plurality of Fast Fourier Transform operations.

14. The method of claim 1, comprising:
transmitting the generated heart-rate signal.

15. A device, comprising:
an interface configured to receive a heart-beat signal and one or more acceleration signals: and
signal processing circuitry coupled to the interface and configured to:
select heart-beat data blocks based on the heart-beat signal;
select acceleration data blocks based on the one or more acceleration signals;
convert the selected heart-beat data blocks to heart-beat frequency domain data blocks;
convert the selected acceleration data blocks to acceleration frequency domain data blocks;
perform motion compensation in the frequency domain based on the converted frequency domain data blocks;
generate an estimated heart rate based on the motion compensation;
generate a predicted estimate based on the acceleration frequency domain data blocks; and
generate a heart-rate signal based on the estimated heart rate and the predicted estimate, wherein a linear function is used to generate the predicted estimate, and the linear function is updated based on the generated heart-rate signal.

16. The device of claim 15, comprising:
one or more light sources; and
one or more optical sensors configured to generate the heart-beat signal.

17. The device of claim 15 wherein the signal processing circuitry is configured to:
multiply the acceleration frequency domain data blocks by respective scalar weights; and
subtract the weighted acceleration frequency domain data blocks from the heart-beat frequency domain data blocks.

18. The device of claim 15 wherein the signal processing circuitry is configured to:
generate a compensated heart-beat signal; and
generate the estimated heart rate based on the compensated heart-beat signal.

19. The device of claim 18 wherein the signal processing circuitry is configured to:
compute a non-linear predictor value based on the acceleration frequency domain data blocks; and
generate the predicted estimate as a linear function of the predictor value.

20. The device of claim 19 wherein the signal processing circuitry is configured to select one of the estimated heart rate and the predicted estimate.

21. The device of claim 19 wherein the signal processing circuitry is configured to: average a plurality of estimated heart rates estimated at different times.

22. The device of claim 20 wherein the signal processing circuitry is configured to:

update said linear function by storing a current estimated heart rate and predictor value when the estimated heart rate is selected, obtaining a sequence of observation points; and
calculate the linear function as a regression over said sequence of observation points.

23. The device of claim 15 wherein the signal processing circuitry comprises:
a plurality of low-pass filters and a plurality of high-pass filters configured to filter the received signals.

24. The device of claim 15 wherein the signal processing circuitry is configured to:
generate a data block based on the received heart-beat signal;
determine whether the generated data block satisfies a testing condition;
when the generated data block satisfies the testing condition, convert the generated data block and data blocks based on the received one or more acceleration signals which are time-aligned with said generated data block to frequency domain data blocks; and
when the generated data block does not satisfy the testing condition, discard the generated data block and generate a new data block that is time-shifted relative to the previously generated data block.

25. The device of claim 15, comprising:
a transmitter coupled to the signal processing circuitry and configured to transmit the generated heart-rate signal.

26. A system, comprising:
an optical sensor, which, in operation, generates a heart-beat signal;
an accelerometer, which, in operation, generates one or more acceleration signals; and
signal processing circuitry communicatively coupled to the optical sensor and the accelerometer, wherein the signal processing circuitry, in operation:
selects heart-beat data blocks based on the heart-beat signal;
selects acceleration data blocks based on the one or more acceleration signals;
converts the selected heart-beat data blocks to heart-beat frequency domain data blocks;
converts the selected acceleration data blocks to acceleration frequency domain data blocks;
performs motion compensation in the frequency domain based on the converted frequency domain data blocks;
generates an estimated heart rate based on the motion compensation;
generates a predicted estimate based on the acceleration frequency domain data blocks; and
generates a heart-rate signal based on the estimated heart rate and the predicted estimate, wherein a linear function is used to generate the predicted estimate, and the linear function is updated based on the generated heart-rate signal.

27. The system of claim 26, comprising:
an integrated circuit including the signal processing circuitry.

28. The system of claim 27 wherein the integrated circuit includes the optical sensor and the accelerometer.

29. The system of claim 26, comprising:
a transmitter configured to transmit the generated heart-rate signal.

30. The system of claim 26, comprising a display.

31. A non-transitory computer-readable medium having contents which configure a heart-rate monitoring device to perform a method, the method comprising:
  selecting heart-beat data blocks based on a received heart-beat signal;
  selecting acceleration data blocks based on one or more received acceleration signals;
  converting the selected heart-beat data blocks to heart-beat frequency domain data blocks;
  converting the selected acceleration data blocks to acceleration frequency domain data blocks;
  performing motion compensation in the frequency domain based on the converted frequency domain data blocks;
  generating an estimated heart rate based on the motion compensation;
  generating a predicted estimate based on the acceleration frequency domain data blocks; and
  generating a heart-rate signal based on the estimated heart rate and the predicted estimate, wherein a linear function is used to generate the predicted estimate, and the linear function is updated based on the generated heart-rate signal.

32. The medium of claim 31 wherein the method comprises:
  multiplying the acceleration frequency domain data blocks by respective scalar weights; and
  subtracting the weighted acceleration frequency domain data blocks from the heart-beat frequency domain data blocks.

33. The medium of claim 32 wherein the method comprises:
  generating a compensated heart-beat signal; and
  generating the estimated heart rate based on the compensated heart-beat signal.

34. The medium of claim 33 wherein the method comprises:
  computing a non-linear predictor value based on the acceleration frequency domain data blocks; and
  generating the predicted estimate as a linear function of the predictor value.

35. The medium of claim 31 wherein the method comprises:
  transmitting the generated heart-rate signal.

* * * * *